US00PP15849P3

(12) United States Plant Patent
Kobayashi

(10) Patent No.: US PP15,849 P3
(45) Date of Patent: *Jul. 12, 2005

(54) *EUPHORBIA* INTERSPECIFIC HYBRID PLANT NAMED 'ECKCORY'

(50) Latin Name: *Euphorbia pulcherrima*× *Euphorbia cornastra*
Varietal Denomination: Eckcory

(76) Inventor: Ruth Kobayashi, 2615 Cazadero Dr., Carlsbad, CA (US) 92009

( * ) Notice: Subject to any disclaimer, the term of this patent is extended or adjusted under 35 U.S.C. 154(b) by 185 days.

This patent is subject to a terminal disclaimer.

(21) Appl. No.: 09/947,586

(22) Filed: Sep. 6, 2001

(65) Prior Publication Data

US 2003/0051284 P1 Mar. 13, 2003

(51) Int. Cl.[7] ..... A01H 5/00
(52) U.S. Cl. ..... Plt./302
(58) Field of Search ..... Plt./302, 303–307

(56) References Cited

U.S. PATENT DOCUMENTS

| | | | | |
|---|---|---|---|---|
| PP4,761 P | | 8/1981 | Stirnadel | Plt./302 |
| 4,724,276 A | | 2/1988 | Ecke, Jr. | 800/1 |
| PP8,735 P | | 5/1994 | Gutbier | Plt./304 |
| PP13,341 P2 | * | 12/2002 | Kobayashi | Plt./303 |
| 6,515,200 B1 | * | 2/2003 | Kobayashi | 800/269 |

OTHER PUBLICATIONS

Dehgan, Phylogenetic significance of interspecific hybridization in *Jatropha* (Euphorbiaceae), *Sytematic Bot.*, 9(4):467–478, 1984.
Dole et al., "Investigations on the nature of a graft–transmissible agent in poinsetta," *Can. J. Bot.*, 71:1097–1101, 1993.
Dolezel et al., "Embryo development and in vitro culture of *Allium cepa* and its interspecific hybrids," *Z Pflanzenzucht*, 85:177–184, 1980.
Dressler, "A new and attractive poinsettia, *Euphorbiaceae*, from Guerrero, Mexico," *Bol. Soc. Bot. Mexico*, 35:17, 1975.
Keller et al., "Interspecific crosses of onion with distant *Allium* species and characterization of the presumed hybrids by means of flow cytometry, karyotype analysis and genomic in situ hybridization," *Theor. Appl. Genet.*, 92:417–424, 1996.
Krauter et al., "Efficent interspecific hybridization in the genus *Helianthus* via 'embryo rescue' and characterization of the hybrids," *Theor. Appl. Genet.*, 82:521–525, 1991.
Le Duc and Albrecht, "Dogwood Poinsettia *Euphorbia cornastra* (Dressler) A. Radcliffe–Smith, A New Floral Pot Crop," *HortScience*, 31:472, 1996.
Lee et al. "Phytoplasma induced free–branching in commercial poinsettia cultivars," *Nat Biotechnol*, 15(2):178–182, 1997.
Sorenson and Brewbaker, "Interspecific compatibility among 15 *Leucaena* species (Leguminosae: Mimosoideae) via artificial hybridizations," *Amer. J. Bot*, 81(2):240–247, 1994.
Suszwik, "The secret of free branching poinsettias," *Beltsville Area Research Highlights: 1998 Reprints from Agricultural Research*, p. 56, 1998.
Co–pending U.S. Appln. No. 09/690,370, filed Oct. 16, 2000.

* cited by examiner

*Primary Examiner*—Kent Bell
*Assistant Examiner*—W C Haas
(74) *Attorney, Agent, or Firm*—Fulbright & Jaworski L.L.P.

(57) ABSTRACT

The variety "Eckcory" is a new and distinct interspecific hybrid plant. The plant is characterized by clean and dark green foliage, eliptical leaves that have acute bases and acuminate tips, brightly colored pink and white brachts and strong lateral branching.

1 Drawing Sheet

CROSS-REFERENCE TO RELATED APPLICATIONS

This application claims the priority of U.S. patent application Ser. No. 09/690,370, filed Oct. 16, 2000.

Botanical classification: *Euphorbia pulcherrima*×*Euphorbia cornastra* insterspecific hybrid.

BACKGROUND OF THE INVENTION

The invention relates generally to the new and distinct variety of interspecific plant termed "Eckcory." The new plant was created in my greenhouse and laboratory in Encinitas, Calif. The plant was prepared by crossing the *Euphorbia pulcherrima* variety "M-6," a Paul Ecke Ranch proprietary variety, with a seedling of the uncultivated species *Euphorbia cornastra.* The variety was selected by excision of a newly formed embryo from a seedpod followed by growth into a plantlet on nutrient agar medium. The cultured plantlet was transplanted to a greenhouse growing-medium, where it developed into the mature plant of the invention. As the plant matured, it exhibited strong terminal dominance with little lateral branch development. To induce lateral branching, the new plant was grafted onto a "selfbranching" rootstock by application of the procedures set forth in U.S. Pat. No. 4,724,276.

The plant of the invention is distinct from the parent plants from which it was derived. For example, *Euphorbia pulcherrima* is a "short day" plant with respect to flower initiation, while *Euphorbia cornastra* is a "long day" plant. However, the interspecific hybrid flowered in response to short days and the time to full flower development was found to be a relatively short six weeks, compared to the *E.*

*pulcherrima* parent that took nine weeks for flower development under the same growing environment.

The first vegetative propagation of the plant in vitro occurred in October, 1998 in Encinitas Calif. The plant was first propagated ex vitro by grafting in August, 1999 in Encinitas, Calif. The distinctive characteristics of the plant remained consistent following propagation.

BRIEF DESCRIPTION OF THE DRAWING

The plant of the invention is illustrated in the accompanying color photographs.

DETAILED DESCRIPTION OF THE VARIETY

The following is a detailed description of the new plant as observed in Encinitas, Calif., USA during May 2000. Observations were recorded from flowering plants, grown as one branched plant per pot. Plants were about 14 weeks from unrooted cuttings when photographs were taken. The pot was 17 cm in diameter and 13 cm in height. Color designations are compared to the 1986 edition of R.H.S. Colour Chart, first published in 1966 by The Royal Horticultural Society, London, England.

| | |
|---|---|
| Origin: | An interspecific hybrid created by cross-pollinating a cultivated *Euphorbia pulcherrima* plant with an uncultivated *Euphorbia cornastra* plant. |
| Classification: | Botanical - *Euphorbia X hybrid* |
| Form: | Shrub |
| Height: | Short–medium |
| Growth Habit: | Flowering was observed, branched plant in a pot with an overall height of 42 cm, including the pot and an overall width of 42 cm. The plant grew upright but was somewhat spreading. The average diameter of the inflorescences, which were primarily composed of colored bracts, was 20 cm. |
| Branching: | Lateral branches develop and terminate in a flower without pinching. However, when pinched before flower induction to remove terminal dominance, all lateral branches develop uniformly and at a faster rate. The plant of description was pinched leaving 12 nodes on the stem. Strong lateral branches of nearly equal length and vigor arose, one from each stem node, resulting in a plant with 12 lateral branches. The lowermost lateral had 14 nodes and the uppermost, 9 nodes subtending the flower. |

-continued

| | |
|---|---|
| Average branch diameter and color: | The average branch diameter was approximately 3 mm, and color was 146C. |
| Growth Rate: | Rooting of stem cutting occurs in 18–21 days under intermittent mist. The plant will flower in about 6 weeks under continuous long night conditions and night temperatures of about 16–18 degrees C. |
| Foliage: | The foliage is clean and dark green from bottom to top of the plant. The leaves are of medium size, leaf blades typically 10 cm long and 5 cm wide for the larger lower leaves and 6 cm long and 2.5 cm wide for the smaller upper leaves. Leaf petioles are green and 6 cm long on the larger leaves to 3 cm on the smaller leaves. The upper leaf surface is glabrous, but slightly rugose and the under surface is finely pubescent. |
| Leaf shape: | Leaves are elliptic with acute bases and acuminate tips. Leaf margins are entire. |
| Leaf arrangement: | Leaf arrangement alternate, single. Petiole length about 4 cm, diameter about 2 mm, color 178B (mature leaf petiole), 146C(immature leaf petiole). |
| Number of Leaves | Typical number of leaves per lateral branch about 12, observed 9 to 14 leaves per lateral branch. |
| Color: | Upper side - Dark green, darker than RHS 139A<br>Under side - Green, near RHS 147B |
| Bracts: | There were 2–4 pink transitional bracts at the upper stem nodes just below the inflorescence. These were 7–8 cm long and 3 cm wide. Eight to 10 bracts subtending the cyathia varied in size from 5 cm long and 2 cm wide to 1.5 cm long and 1 cm wide. |
| Shape: | Bracts are elliptic with acute bases and acuminate tips. Bract margins are entire. |
| Color: | Upper side - Pink, near RHS 57D<br>Under side - Grayish-White, near RHS 156D |
| Flowers: | Generally, 8–10 rudimentary and sterile cyathia (flowers) were present at maturity. Each cyathium was about 5 mm long and 3 mm wide and green in color. |
| Pathogen resistance: | Resistance to pathogens and pests common to *E. pulcherrima* or *E. cornastra* has not been observed on plants grown under commercial conditions. |

What is claimed is:

1. A new and distinct *Euphorbia* interspecific hybrid plant variety named "Eckcory" as illustrated and described herein.

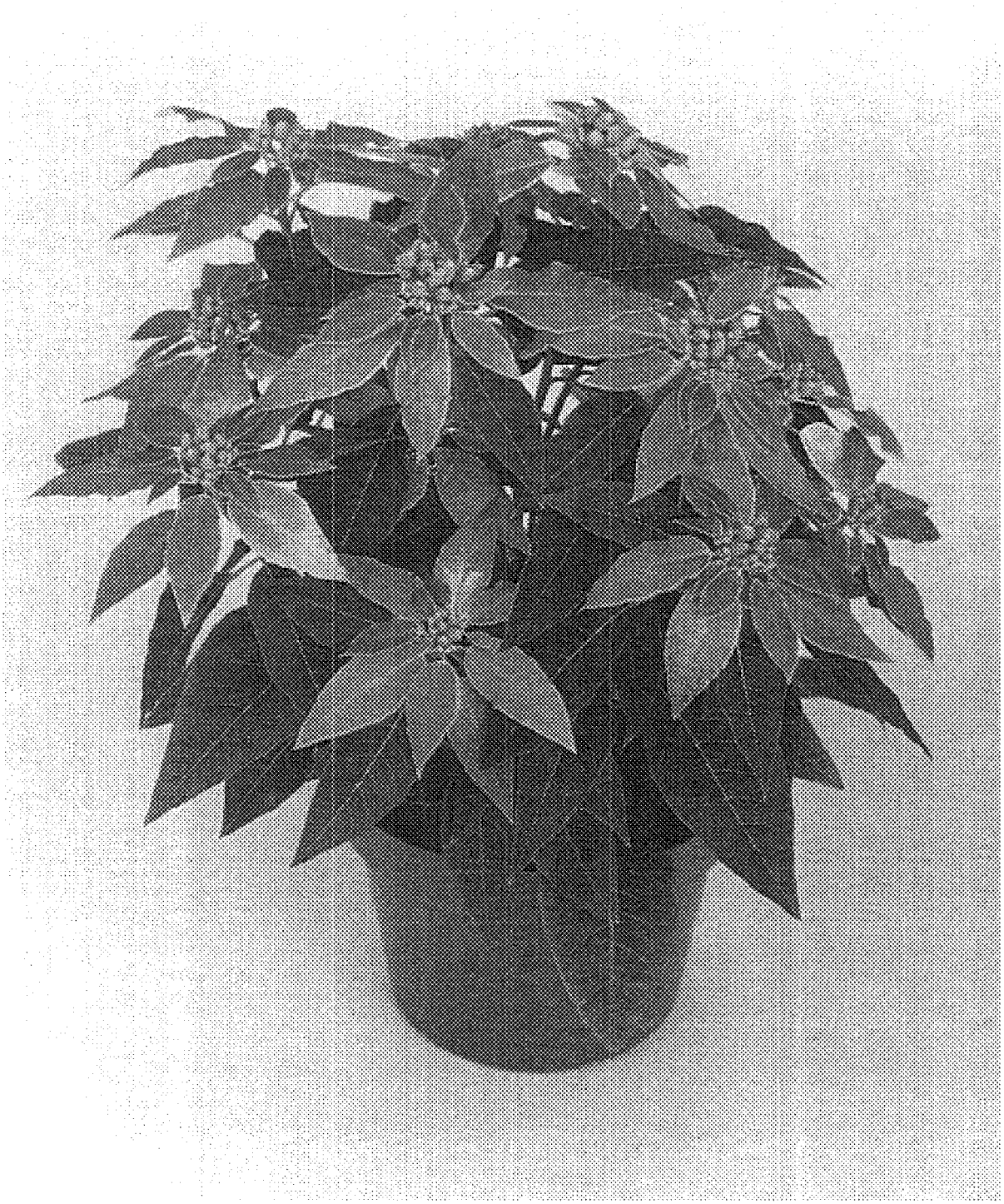

* * * * *